United States Patent [19]

Sekiguchi et al.

[11] Patent Number: 5,366,766
[45] Date of Patent: Nov. 22, 1994

[54] METHOD OF MANUFACTURING THIN FILM AND THIN FILM DEVICE

[75] Inventors: Atsushi Sekiguchi; Nobuo Shimo, both of Chiba, Japan

[73] Assignee: Research Development Corporation of Japan, Tokyo, Japan

[21] Appl. No.: 860,020

[22] Filed: Mar. 30, 1992

[30] Foreign Application Priority Data

May 10, 1991 [JP] Japan .................. 3-105496

[51] Int. Cl.$^5$ .............................................. C23C 16/04
[52] U.S. Cl. .................. 427/255.4; 427/255.6; 427/261
[58] Field of Search ............. 427/302, 261, 255.4, 427/255.6, 99, 295

[56] References Cited

U.S. PATENT DOCUMENTS

| | | | |
|---|---|---|---|
| 4,179,532 | 12/1979 | Soeding | 427/302 |
| 4,196,033 | 4/1980 | Arai et al. | 427/264 |
| 4,241,112 | 12/1980 | Kostandov et al. | 427/302 |
| 4,268,541 | 5/1981 | Ikeda et al. | 427/177 |
| 4,448,803 | 5/1984 | Ganger et al. | 927/115 |
| 4,536,468 | 8/1985 | Yasui et al. | 427/51 |
| 4,699,804 | 10/1987 | Miyata et al. | 427/302 |
| 4,743,468 | 5/1988 | Ronn et al. | 427/99 |

OTHER PUBLICATIONS

Applied Physics Letters, vol. 59, 4 Nov. 1991, No. 19, pp. 2466–2468, A. Sekiguchi et al., "Micrometer patterning of phthalocyanines by selective chemical vapor deposition".

Journal of Vacuum Science & Technology A, Second Series, vol. 10, No. 4, Part II, Jul./Aug. 1992, pp. 1508–1510, A. Sekiguchi et al., "Micrometer Patterning of phthalocyanine derivatives by selective chemical vapor deposition method".

*Primary Examiner*—Shrive Beck
*Assistant Examiner*—Diana Dudash
*Attorney, Agent, or Firm*—Wenderoth, Lind & Ponack

[57] ABSTRACT

Introducing a raw material organic substance onto a substrate surface, causing polymerization of the raw material organic substance on the substrate surface and causing deposition of the resultant polymer on the substrate surface, previously forming a pattern on the substrate surface with at least two kinds of substances and/or through surface modification, and selectively forming an organic thin film only on this pattern or only on a portion other than the pattern. By this procedure, it is possible to directly deposit and form a thin pattern of an organic thin film, such as a film having a thickness up to 10 μm.

6 Claims, 5 Drawing Sheets

METHOD OF MANUFACTURING THIN FILM AND THIN FILM DEVICE

FIELD OF THE INVENTION

The present invention relates to a method of manufacturing a thin film and a thin film device. More particularly, the present invention relates to a new method of manufacturing which permits formation of an organic polymer thin film having a prescribed pattern and a to a functional electron-optical thin film device based on the application of this method.

PRIOR ART

Along with the rapid progress of the structure of devices such as semiconductor elements, various sensors, display elements, light receiving/emitting elements, optoelectric transducers and photochemical functional elements, there is an increasing demand for the use of organic thin films having fine patterns.

The productions of such organic thin films is considered important as an intermediate step towards the production of devices having more sophisticated sophistication of device functions and is considered an important approach leading to the production of molecular devices.

However, according to the conventional dry-type film manufacturing processes, such as vacuum deposition, sputtering, CVD, photo-CVD, laser CVD, HOMOCVD, MOCVD, MEB, ICB and iron plating, it was considered impossible to produce such a thin film from an organic polymer having a low vapor pressure, while directly patterning it.

Some methods of forming a thin film with an organic substance as a raw material have, of course, been known, such as, the CVD method in a semiconductor manufacturing process. This method comprises decomposing a raw material substance having a relatively high vapor pressure, thus causing deposition of a metal or a semiconductor having a low vapor pressure. This method does not, however, make it possible to form a thin film having a low vapor pressure.

As a method of manufacturing an organic thin film through a dry-type process, vacuum deposition, including an MBE method, is known. This is usually employed as a technique to form a thin film without changing the molecular structure of the raw material, and recently research efforts have been extensively carried out in respect to porphyrin the formation of such films by use of and phthalocyanine. This method is however defective in that high-temperature conditions are indispensable upon evaporation as the vapor pressure of the raw material substance becomes lower, and this causes deterioration of the raw material substance. For this reason, this method is not suitable for the formation of a thin film from an organic substance having a low vapor pressure.

The vaporization-polymerization method is known as a method used to solve the above-mentioned problems. This method comprises causing vaporization of molecules of a monomer having a low vapor pressure and causing polymerization-deposition onto a prescribed surface to be treated. K. Tanaka, et al. propose examples of aliphatic polyamide (nylon) in their report appearing in Prog. Polymer. Phys. Jpn., Vol. 30, p. 175 (1987), and Okui, et al. have reported examples of polyimide in Nikkan Kyogyo Shinbun, Feb. 21, 1991. As a method of using polyphthalocyanine, M. Yudasaka has reported the dual source vaporization method in Jpn. J. Appl. Phys., Vol. 24, p. L887 (1985).

Examples using a CVD process are reported, for example, by M. Ashida, et al. in J. Polymer Sci., A. Polymer Chem., vol. 27, p. 3883 (1986) and by H. Yanagi, et al. in Bull. Chem. Soc. Jpn., Vol. 61, p. 2313 (1988), and the references cited therein.

In these methods, however, a film is deposited over the entire surface to be treated, and it is impossible to directly manufacture a fine pattern of, for example, up to 10 $\mu$m.

More specifically, a patterned thin film of up to 10 $\mu$m is essential in general for the production of an integrated circuit. In the process of manufacturing an integrated circuit, a light-sensitive polymer photoresist is used as a technique to pattern a thin film. The film of an ordinary metal, a semiconductor or an insulator is etched with this photoresist as a mask, thus obtaining a target pattern.

Naturally therefore, it is impossible to used the photoresist as a mask, and because the organic thin film is damaged by the organic solvents used for, developing and peeloff of the photoresist and even by the photoresist itself. Thus, according to the procedure, it is not possible to obtain a micrometer scale patterned of the organic thin film.

It was therefore impossible, by the application of the conventional technique, to manufacture a thin film device having by use of a patternized structure of up to $\mu$m of, for example, a phthalocyanine derivative.

This phthalocyanine derivative is conventionally known to have the nature of a p-type semiconductor as a system of photoelectric conductivity and photochemical energy transfer, and trials have been made to use it as a gas sensor and for photodiodes. However, phthalocyanine derivative exhibited a low response speed and a low resolution, and was not at all practical.

Under such circumstances, there is a strong demand for the development of a new process or technique permitting formation of an organic thin film through direct deposition in the form of a pattern.

SUMMARY OF THE INVENTION

The present invention provides, as a means to solve the above-mentioned problems, a method of manufacturing a thin film, which comprises the steps of, when introducing a raw material organic substance into the front space of the surface of a substrate, causing polymerization of the raw material organic substance on the substrate surface and/or in the front space of the substrate surface, and depositing the resultant polymer on the substrate surface, previously patterning the substrate surface with at least two kinds of substances and/or through surface modification, and forming a thin film of an organic substance only on this pattern or on the portion other than said pattern.

The present invention provides also embodiments wherein the formed organic thin film is heat-treated under vacuum or in a prescribed gaseous atmosphere, or if formed through a condensation polymerization reaction or a non-condensation polymerization reaction of the organic substance.

The symbols in the drawings are defined as follows;
1. Substrate
2. Thin film
10. Raw material organic substance
12. Sample bin
20. Test tube
30. Electric arc furnace
50. Organic thin film
51. Heat-treated organic thin film
52. Organic thin film prepared under non-selective condition (300° C.)
70. Glass substrate
71. Copper thin film
72. Chromium thin film
73. Gold thin film
75. Organic thin film

DETAILED DESCRIPTION OF THE INVENTION

In the present invention, any of various raw material organic substances may be used.

The organic substance is preferably selected from organic materials having various functional groups which are able to react or combine with patterned or modified substrate surface materials, under the condition of polymerization or deposition of the organic substance.

Many kinds of organic materials having functional groups, such as cyano derivatives including phthalocyanine derivatives, quinone derivatives, azo derivatives, hydrazine derivatives, hydrazido derivatives, isocyanate derivatives, halogeno derivatives, nitro derivatives, amino derivatives, hydroxy derivatives, carbonyl derivatives, carboxyl derivatives, alkoxyl derivatives, olefinic derivatives, hetero-cyclic functional derivatives, etc., can be typically used.

The substrate substance or modified substrate substance reacts or combines with organic substances catalytically, when such organic substances are polymerized or deposited.

In the present invention, an insulator or a semiconductor may be used as the substrate, and the pattern on the substrate may be formed with a metal. For example, silicon or sapphire may be used as the substrate, and one or more of copper, gold, silver, zinc, tin, lead, manganese, cadmium, tantalum, niobium, molybdenum, tungsten, titanium, zirconium, gallium, chromium, iron, nickel and cobalt may be used as a metal or alloys thereof any.

This method enables the art-skilled to deposit an organic polymer thin film on a pattern previously formed on a substrate with at least two kinds of substances and/or through surface modification, or deposit on a portion other than the pattern, and use to use it as a unique thin film device.

The thin film device using the phthalocyanine derivative patterned into a size of up to 10 $\mu$m, as part of the configuration, permits achievement of a high-speed response or a high resolution.

In the present invention, by previously patterning the surface of a substrate with at least two kinds of substances and/or through surface modification, a polymerization reaction generating a prescribed deposition film is selectively induced from the differences in properties of the substrate surface, thus manufacturing a target patterned organic thin film. By means of the patterned organic thin film thus manufactured by this method, a thin film device giving a high-speed response or a high resolution is achieved.

EXAMPLES

Now, the method of the present invention is described further in detail with reference to the attached drawings.

EXAMPLE 1

Figure 1:
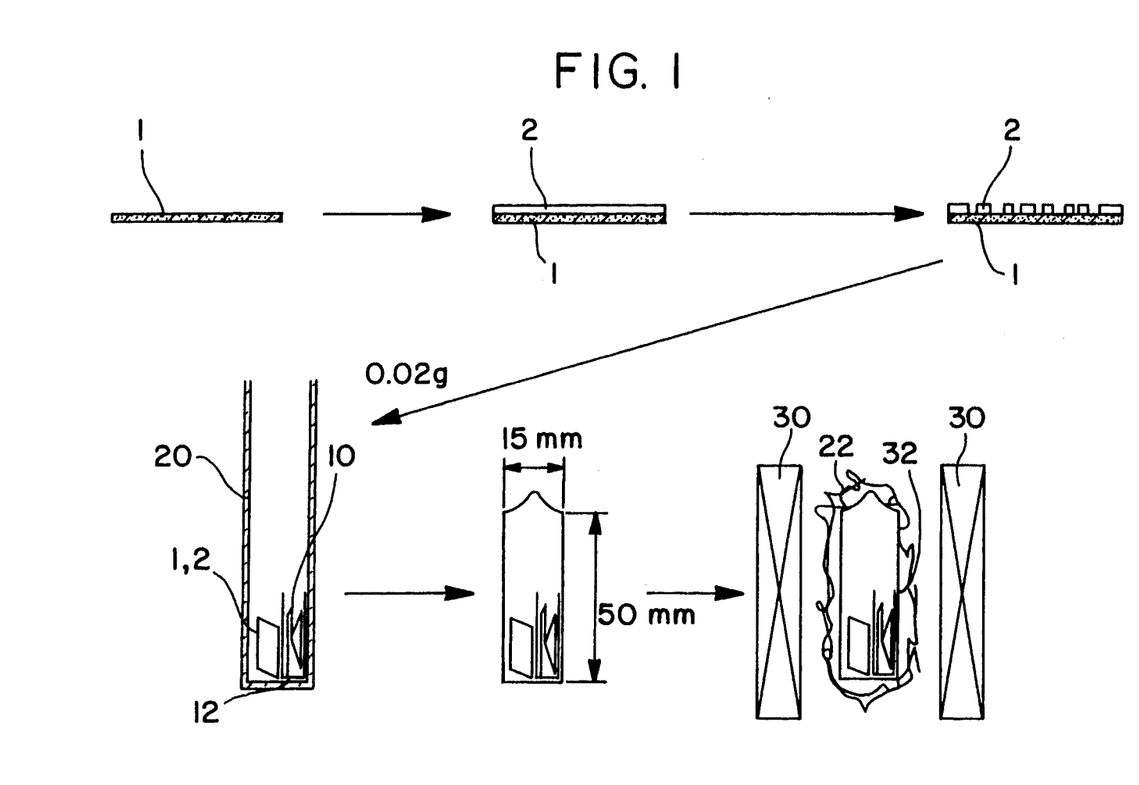
FIG. 1 is a process sectional view illustrating an embodiment of the method of manufacturing a thin film of the present invention.

FIG. 1 illustrates an example of the method of manufacturing a thin film of the present invention.

As shown in FIG. 1, the method of the present invention is applied in the form of the following process:

(a) Pretreatment of substrate:

A mirror-surface copper thin film (2) in an amount of 400 nm is formed on the silicon substrate (1) washed with 1% hydrogen fluoride by the high-frequency magnetron sputtering method while water-cooling the substrate (1).

This thin film (2) is a polycrystal film showing a weak orientation in (100) and (111) planes.

Then, a photoresist (MICROPOSIT S1400-27 manufactured by Shipley Fareast Co.) is spin-coated into a thickness of approximately 1 $\mu$m on the surface of the copper thin film (2), and after soft-baking the thus coated substrate at a temperature of 105° C. for 45 seconds, a pattern of a micrometer order is exposed on this photoresist by means of a contact exposure device. After the completion of exposure, development is performed with a development liquid (MF-319 manufactured by Shipley Fareast Co.). With the thus patterned photoresist as a mask, the copper thin film (2) is wetted with ferric chloride-hydrochloric acid solution. Subsequently, the photoresist is peeled off with the use of a resist peeling liquid and acetone vapor. After water-rinsing, drying is rapidly carried out with a spin dry. A pattern of the copper thin film (2) is thus obtained.

(b) Preparation of raw material organic substance:

A raw material organic substance (19) was prepared by sublimation-refining 1, 2, 4, 5-tetracyanobenzene hereinafter abbreviated as "TCNB") (manufactured by Wako Pharmaceutical Co., Ltd., special class reagent) under a pressure of up to $3 \times 10^{-6}$ Torr. This raw material organic substance (10) in an amount of 0.02 g is taken in a glass sample bin (12) having a length of 36 mm and a diameter of 8 mm. This sample bin (12) communicates with the open air through a hole having a diameter of 4 mm.

(c) Preparation of organic thin film:

The above-mentioned sample bin (12) containing the raw material organic substance (10) and the substrate (1) (approx. 8 mm × 12 mm rectangular) having the abovementioned patternized copper thin film (2) deposited thereon are charged in a glass test tube (20) having a length of 150 mm and a diameter of 15 mm.

After evacuating and flushing the test tube (20) three times with argon gas, the tube (20) is sealed under vacuum of up to $5 \times 10^{-6}$ Torr to achieve a length of approximately 50 mm. The test tube (20) is wrapped by aluminum foil (22) and heated in an electric arc furnace (30). Temperature control of this electric arc furnace (30) is carried out by measuring the temperature of the test tube (20) by means of a thermocouple (32) installed on the aluminum foil (22) and adjusting power to the electric arc furnace (30) by thyristor by means of a PID controller. After heat-treating the test tube (20) in the electric arc furnace (30) at a prescribed temperature for a prescribed period of time, the test tube (20) is taken out the electric arc furnace (30) and left to cool down to the room temperature. Then, the test tube (20) is softly broken to take out the substrate (1).

Figure 6:
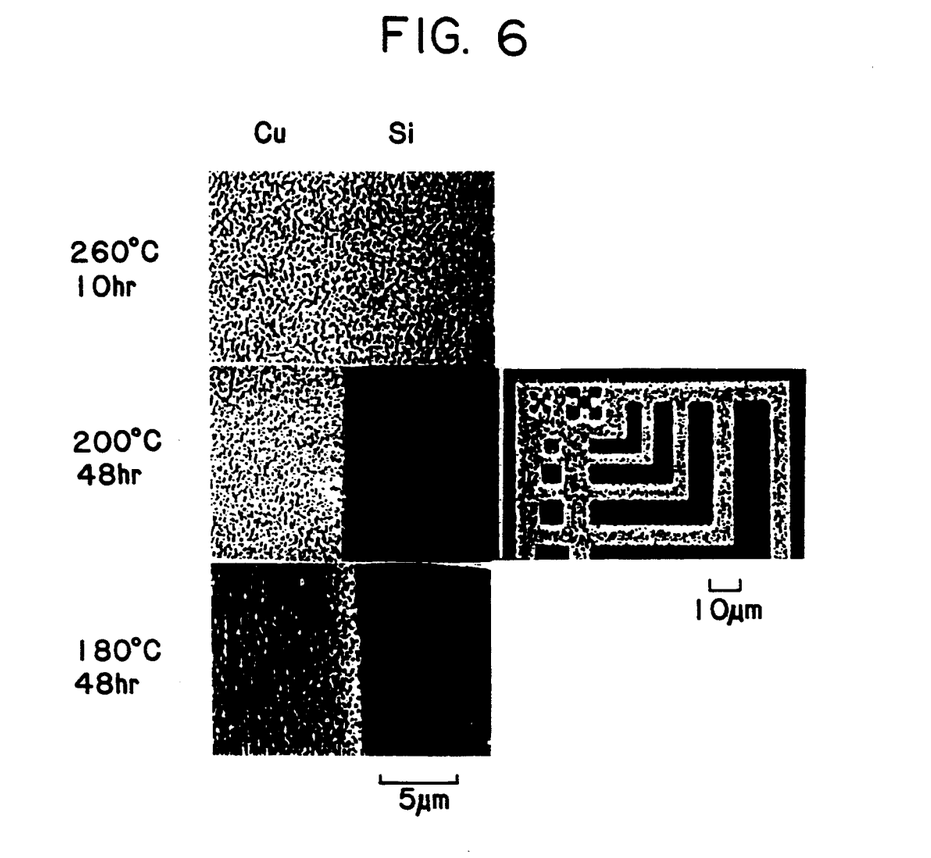
FIG. 6 is a status observation view illustrating the state of the substrate surface in the method shown in FIG. 1.

The surface condition of this substrate (1) is shown in FIG. 6 (20 KV×5,000 and 20 KV×1,000). No deposition of the organic thin film (50) is observed on the silicon surface at a treatment temperature of under 260° C., but this organic thin film (50) is deposited on the copper surface. At a temperature of at least 200° C., on the other hand, deposition of an organic thin film (50) is observed on the surface of both silicon and copper. This reveals that it is important for pattern formation to conduct treatment at a temperature of under 260° C.

The available size of the pattern is dependent on the current level of wet etching technique of copper, and it is possible to directly form a fine pattern of from 1 to 2 μm of the organic thin film.

It is needless to mention that the use of a finer patternization technique of copper (such as dry etching) would permit direct formation of a pattern of the organic thin film (50).

Figure 2:
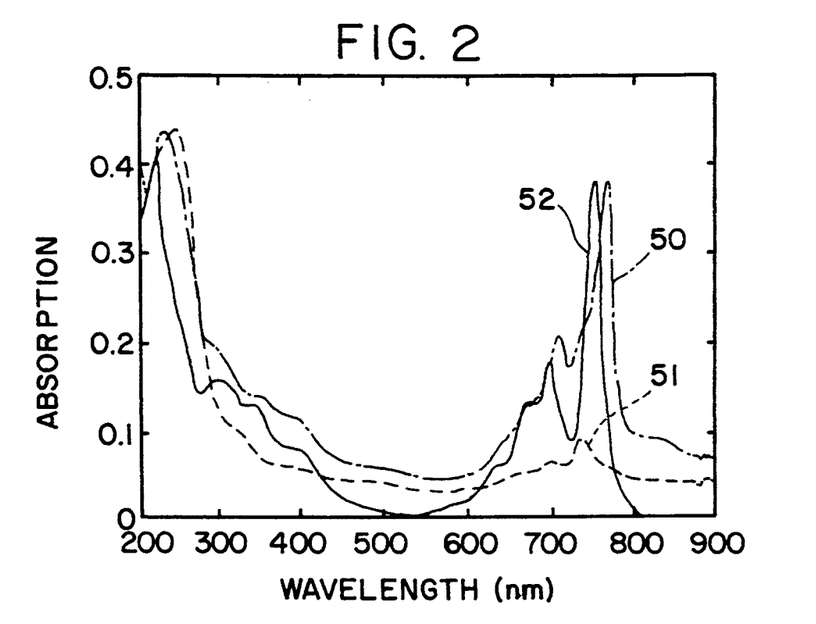
FIG. 2 is an absorption spectrum diagram of visible ultraviolet ray as measured after dissolution of a formed organic thin film into concentrated sulfuric acid.

To observe the structure of the thus obtained organic thin film (50), the organic thin film (50) prepared at a treatment temperature of 200° C. for 48 hours was dissolved into concentrated sulfuric acid, and the visible ultraviolet absorption spectrum of the resultant solution is illustrated in FIG. 2. The spectrum is known to be that of a phthalocyanine derivative, though slightly shifting toward the longer wavelength side. This suggests that four molecules of the raw material organic substance (10), TCNB, form a phthalocyanine ring through polymerization. Furthermore, polyphthalocyanine may be produced from the polymerization of octocyanophthalocyanine resulting from the four-molecule polymerization of TCNB.

Figure 3:
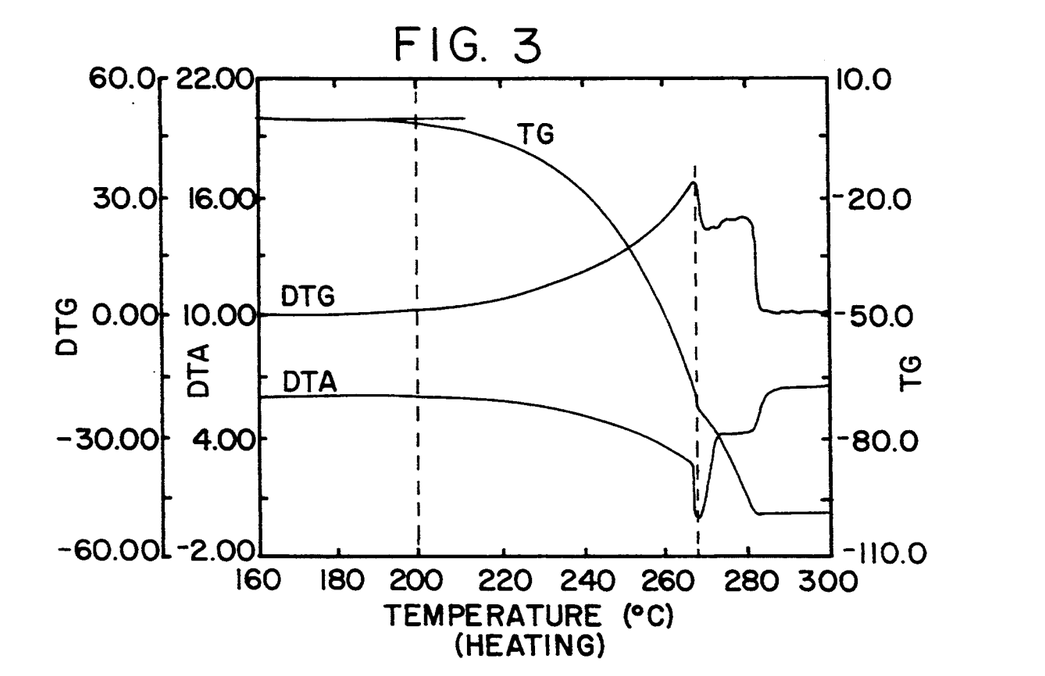
FIG. 3 is a measurement diagram of thermal weight analysis and differential thermal analysis of TCNB of a raw material organic substance.

FIG. 3 illustrates the results of a thermal weight analysis TG and differential thermal analysis DTA of TCNB, which is the raw material organic substance (10). Effective deposition was observed at temperatures of at least 180° C., at which effective sublimation of the raw material organic substance (10) was observed at temperatures lower than the melting point (269° C.) of the (see FIG. 6). The sublimated raw material organic substance (10) is considered to diffuse on the surface of the substrate (1) and into the front space thereof, thus inducing polymerization reaction.

By using the method of the present invention, as described above, it is possible to achieve a selective organic polymerization type CVD method and to deposit a target organic thin film (50) of polymer on the prescribed surface of the substrate while patternizing the same.

EXAMPLE 2

Figure 4A:
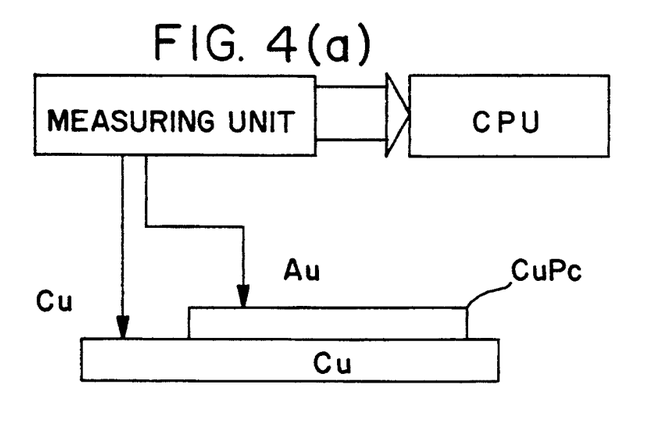
FIG. 4(a) and 4(b) are a sectional view and a resistance measurement diagram, respectively, illustrating the method of electrical measurement of a formed organic thin film and the results of measurement.
Figure 4B:
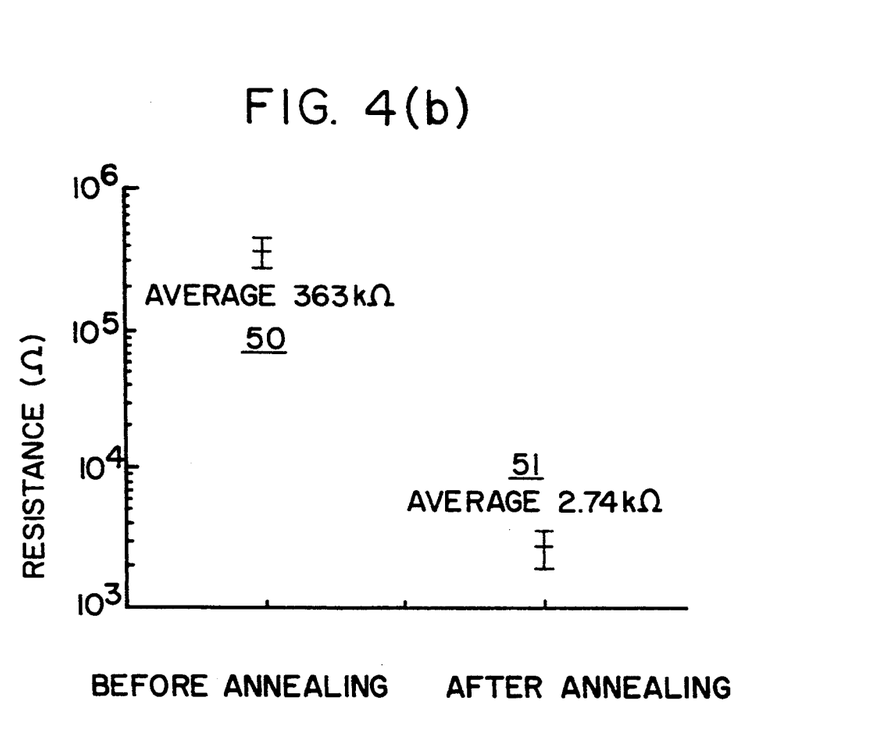

The substrate (1) on which the organic thin film (50) patternized by the method of the above-mentioned Example 1 had been deposited was heat-treated under vacuum of up to $1 \times 10^{-5}$ Torr at 500° C. for three hours. It was possible to prepare a heat-treated organic thin film (51) having an electric resistance decreased by two digits from that of the organic thin film (50). The method and the results of measurement are shown in FIGS. 4 (a) and (b). In this case, the pattern of the organic thin film (50) was maintained. If the temperature of the substrate (1) is increased during preparation of the organic thin film (50) as described above, the target patternization of the organic thin film cannot be accomplished. However, the pattern of the organic thin film (50) can be maintained, even when a heat treatment is applied after deposition of the organic thin film (50) in the once patternized state. It was also possible to reform the organic thin film (50) and thus to prepare the heat-treated organic thin film (51).

The visible ultraviolet absorption spectrum of the solution resulting from the dissolution of the heat-treated organic thin film (51) into concentrated sulfuric acid as in the Example 1 (the film is hardly soluble such that it is necessary to use ultrasonic waves for a long period of time to dissolve it) is shown in FIG. 2. As compared with the state before the heat treatment, the absorption intensity of the Soret band near 250 nm shows no remarkable change, but that of the Q band decreases near 700 Nm. This is considered to suggest that octocyanophthalocyanine was further polymerized under the effect of heat treatment. This inference agrees well with the decrease in electric resistance.

This method of once causing deposition of the organic thin film in the patternized state, and then applying the heat treatment means that is possible to control the quality of organic thin film, while maintaining the pattern, and is therefore an industrially very useful technique. The heat treatment may be applied, not only in a vacuum atmosphere, but also in nitrogen or an inert gas. When weakly applying the heat treatment in oxygen, ozone, or nitrogen oxide, furthermore, the organic thin film is oxidized and resistance of the film decreases. Thus, oxidation is only an example, and heat treatment in any other active gas is also industrially useful.

In the Examples 1 and 2, the cyanobenzene derivative is used as the raw material organic substance (10). This cyanobenzene derivative may be any of the derivatives, such as dicyanobenzene, tricyanobenzene and tetracyanobenzene in which two to four cyano groups are introduced into the benzene ring, derivatives in which one or more hydrogen atoms of these compounds are replaced by a halogen, nitro group, amino group, amide group, hydroxy group, cyano group, carbonyl group, carboxyl group, alkyl group, methoxy group, ethoxy group, alkenyl group or aryl group. By using any of these derivatives, it is possible to achieve the selective organic polymer type CVD method, and to manufacture the thin film through deposition, while patternizing, the target organic polymer thin film on the prescribed substrate surface. Even when the heat treatment was applied after deposition of the organic thin film in the once patternized state, it was possible to maintain the pattern of the organic thin film, and to reform the organic thin film.

EXAMPLE 3

In the Examples 1 and 2, silicon was used as the substrate. By using sapphire, quartz or glass, selectivity was available relative to the copper pattern with the same operations under the same conditions at a temperature under 200° C. More specifically, no deposition of the organic thin film was observed on the surface of sapphire, quartz or glass as on the surface of silicon. Furthermore, even when the heat treatment was applied after deposition of the organic thin film on copper in the once patternized state, it was possible to maintain the pattern of the organic thin film and to reform the organic thin film.

EXAMPLE 4

It was possible to obtain selectivity and achieve the same effects as in the case of copper with the same operations under the same conditions at a temperature of under 200° C. even when any or both of zinc and lead was used in place of copper used in the Examples 1 and 2. Even when applying the heat treatment after deposition of the organic thin film on any or both of zinc and lead in the once patternized state, it was possible to maintain the pattern of the organic thin film and reform the organic thin film.

EXAMPLE 5

Figure 5:
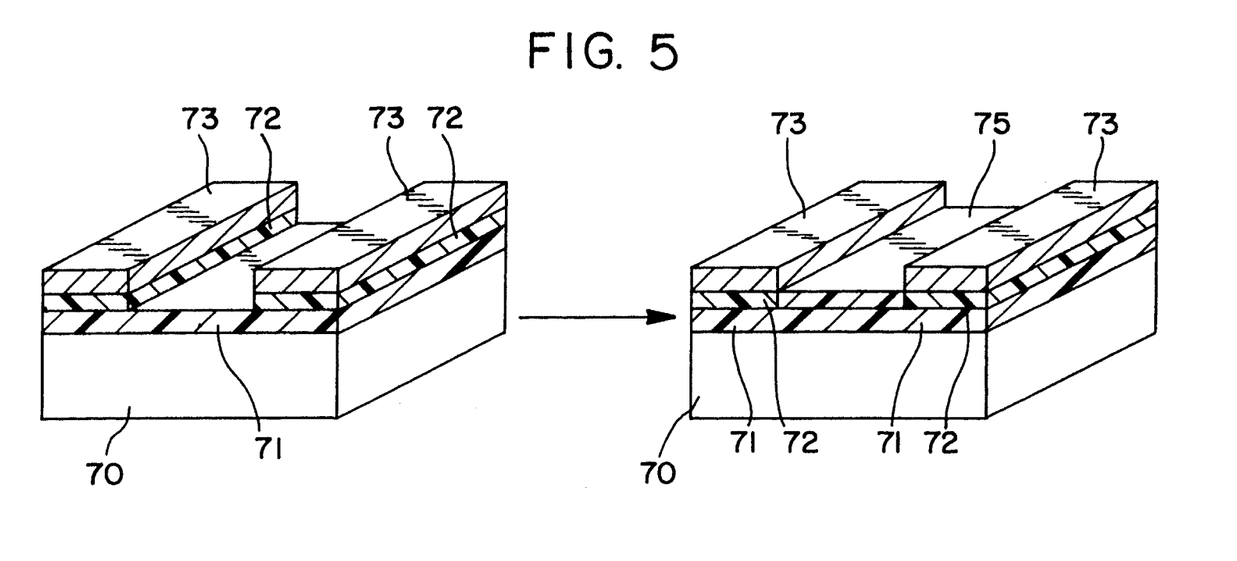
FIG. 5 is a process sectional view illustrating another embodiment of the present invention.

As shown in FIG. 5, a patternized copper thin film (71) (thickness; 50 nm) is manufactured as in the Example 1 with a glass substrate (70) as the base. A chromium thin film (72) of a prescribed pattern in a thickness of approximately 100 nm is formed on the substrate by high-frequency magnetron sputtering in accordance with the lift-off method. A gold thin film (73) of the same pattern in a thickness of approximately 300 nm is formed on the chromium thin film (72) by high-frequency magnetron sputtering.

The method of preparing this film is as follows. As in the Example 1, a sample bin containing a raw material organic substance, and the substrate (approx. 8 mm×12 mm rectangular) on which the patternized copper thin film (71), the chromium thin film (72) and the gold thin film (73) have been deposited are charged in a glass test tube having a length of 150 mm and a diameter of 15 mm.

After evacuating and flushing the interior of the test tube, three times with argon gas, it is vacuum sealed so as to give a length of approximately 50 mm under the pressure of up to $5\times10^{-6}$ Torr. The test tube is wrapped with aluminum foil and heated in an electric arc furnace. The temperature of this electric arc furnace is controlled by measuring the temperature of the test tube with a thermocouple installed on the aluminum foil, and adjusting the power to the electric arc furnace, through a thyristor by means of a PTD controller. The test tube is heat-treated in the electric arc furnace at a prescribed temperature for a prescribed period of time. Then, the test tube is taken out the electric arc furnace and left to cool down to the room temperature. The test tube is softly broken to take out the substrate contained in it.

While deposition of an organic thin film is not observed on the surface of the glass substrate (70) or the gold thin film (73) at a treatment temperature of under 200° C., only the growth of a selective organic thin film on which an organic thin film (75) was deposited was confirmed only on the surface of the copper thin film (71).

The available size of the pattern is dependent on the current level of wet etching technology of the copper thin film (71) and lift-off technology for the preparation of the gold thin film, and it was possible to directly form a pattern of the fine organic thin film (75) of 1 to 2 μm. By using the patterning technique (such as dry etching) of a finer copper thin film (71), it is of course possible to directly form a pattern of a finer organic thin film (75).

When causing direct deposition of the gold thin film (73) on the copper thin film, mutual diffusion between copper and gold rapidly takes place upon heat treatment for the preparation of the prescribed organic thin film (75) and upon heat treatment for the reforming of the organic thin film applied as required. These cannot therefore be employed. A chromium thin film (72) is placed between the cooper thin film (71) and the gold thin film (73). By placing the chromium thin film (72), it is possible to prevent mutual diffusion between the copper thin film (71) and the gold thin film (73).

In the above-mentioned Examples, the substrate has been described as a sheet-shaped article, but it may of course be spherical or of any other shape.

As described above, temperature of the electric arc furnace is controlled by measuring the test tube temperature by a thermocouple installed on the aluminum foil and adjusting the power to the electric arc furnace with a thyristor by means of a PID controller. However, the method of controlling the temperature is not limited to this method and any method may be used as, so long as temperature can be accurately controlled. Thus a simple on/off control without using a PID controller or a thyristor is also acceptable. The heat treatment is also not limited to that based on an electric arc furnace, but light heating using a halogen lamp or high-frequency microwave heating are also applicable. An ordinary method of heat treatment may also be used.

When introducing a raw material organic substance, it is useful from the point of view of controllability to separate the treatment room for treating the substrate from a sublimation room for treating a raw material organic substance and to install a valve at the junction. In this case, it is also useful to transfer a carrier gas from the sublimation room of raw material organic substance to the treatment room of substrate. The system may be, not only a closed pipe system such as a vacuum-sealed one, but also on open pipe system in which air tightness with the open air is well maintained.

Aluminum, scandium, titanium, vanadium, manganese, iron, cobalt, nickel, gallium, tin, indium, cadmium, silver, palladium, ruthenium, molybdenum, niobium, zirconium, hafnium, osmium, platinum, or thallium may be used in place of copper, zinc or lead.

EXAMPLE 6

A micrometer-order pattern of a polyimide thin film is formed with light-sensitive polyimide on the surface of a sapphire substrate by the use of the photographic technology.

Then, the substrate is placed in an aqueous ammonia solution to apply a heat treatment. Then, vaporization polymerization of adipic acid and hexamethylenediamine permits the deposition of an organic thin film, which is a nylon thin film, through condensation polymerization, only on the portion of the surface where a polyimide pattern is not existent.

In the present invention, as described above, a raw material organic substance is introduced onto the surface of a prescribed substrate or into the front space thereof, and the raw material organic substance is polymerized on the substrate surface or in the front space thereof, thereby causing deposition of the polymer on the substrate surface by the utilization of the difference in vapor pressure between the raw material organic substance and the polymer. In this case, it is possible to prepare the thin film only on the prescribed pattern or only on the portion other than the pattern, by previously patterning the substrate surface with two or more substances and/or through surface modification. The apparatus and configuration of materials for this purpose are not limited to those described in the above-mentioned Example.

EXAMPLE 7

A gas sensor was manufactured with the use of the structure shown in FIG. 5. With the gold thin films (73) at the both ends as electrodes, resistance between the both electrodes is monitored. The portion of the phthalocyanine derivative film shows a resistance of several kilo ohms. When this portion comes into contact with nitrogen dioxide, resistance between the both electrodes becomes smaller, thus serving as a sensor of nitrogen dioxide. The gap between the both electrodes is closely related with the sensing speed; a gap of the order of 100 $\mu$m does not permit use even for minutes. However, with a pattern of several um, smaller than 10 $\mu$m, a sensing speed higher than a second was available.

EXAMPLE 8

The structure shown in FIG. 5 can similarly be used as a light sensor.

With the gold thin films (73) at the both ends as electrodes, resistance between the both electrodes is monitored. The portion of the phthalocyanine derivative film shows a resistance of several kilo ohms. When light is irradiated onto this portion, resistance decreases, thus permitting monitoring of the amount of light. Structures as shown in FIG. 5, manufactured in a micro-meter-order of up to 10 $\mu$m, arranged transversely may be used as a high-resolution photodiode array. A two-dimensional arrangement of such structures serves as a high-resolution image sensor. For these photodiode arrays and image sensors, a higher degree of integration leads to a better resolution, thus making them more useful.

In addition, phthalocyanine derivatives are known for their properties as p-type semiconductors and as systems for photochemical energy transfer. The micrometer-order patternizing technology of up to 10 $\mu$m of phthalocyanine derivatives achieved by the present invention is industrially useful.

The thin film device of a phthalocyanine derivative containing a fine pattern of up to 10 $\mu$m, made available by the method of the present invention is also industrially useful as semiconductor elements, various sensors, display elements, light-receiving elements, photoelectric tranducers, photochemical functional elements and organic non-linear material elements.

According to the method of the present invention, as described above in detail, it is possible to directly deposit and form an organic thin film into a pattern by the utilization of the patterned property of the substrate surface, thus permitting formation of a pattern of up to 10 $\mu$m of an organic thin film having prescribed functions.

The thin film device containing a fine pattern of up to 10 $\mu$m of a phthalcoyanine derivative, made available by the method of the present invention, permits achievement of such functions as a high-speed response and high resolution.

What is claimed is:

1. A method of selectively forming a polymer film of a cyano-benzene compound or a derivative thereof on a patterned layer of copper or copper alloy which is disposed upon a surface of a silicon or sapphire substrate without formation of the polymer film on the silicon or sapphire substrate, which method comprises:

contacting said patterned layer with a vapor of a polymerizable cyano-benzene compound or a derivative thereof having cyano groups which react with the copper or copper alloy patterned layer, said contacting being carried out under conditions sufficient to selectively react the cyano groups of the cyano-benzene compound or derivative with the copper or copper alloy without reacting the cyano groups with the silicon or sapphire substrate and under conditions sufficient to polymerize the cyano-benzene compound or derivative which is reacted with the copper or copper alloy layer, whereby a polymer film of said cyano-benzene compound or derivative is obtained which is selectively formed on said copper or copper alloy patterned layer of the silicon or sapphire substrate.

2. A method as claimed in claim 1, wherein said cyano-benzene compound or said derivative thereof is polymerized and reacted by being heat-treated under vacuum or in a gaseous atmosphere.

3. A method as claimed in claim 1, wherein said polymer film is formed through condensation polymerization reaction of the cyano-benzene compound or said derivative thereof.

4. A method as claimed in claim 1, wherein said polymer film is formed through non-condensation polymerization reaction of the cyano-benzene compound or said derivative thereof.

5. A method as claimed in claim 1, wherein said polymer film is formed by at least four molecules of the cyano-benzene compound or said derivative thereof.

6. A method as claimed in claim 1, wherein said polymer film is formed by a phthalocyanine derivative.

* * * * *